United States Patent [19] [11] 4,000,170
Forster et al. [45] Dec. 28, 1976

[54] PRODUCTION OF CARBOXYLIC ACIDS BY CONTROLLING THE ACTIVE FORM OF IRIDIUM CATALYST IN RESPONSE TO INFRARED ABSORPTION SPECTRA

[75] Inventors: Denis Forster, University City; Arnold Hershman, Creve Couer; Donald E. Morris, Kirkwood, all of Mo.

[73] Assignee: Monsanto Company, St. Louis, Mo.

[22] Filed: July 29, 1974

[21] Appl. No.: 492,957

[52] U.S. Cl. ............................ 260/413; 23/230 R; 260/514 M; 260/533 A; 423/417
[51] Int. Cl.$^2$ ........................................ C07C 51/14
[58] Field of Search ........ 260/413, 514 M, 533 AN, 260/533 A; 23/230 R; 423/416, 417, 418

[56] References Cited
UNITED STATES PATENTS

| | | | |
|---|---|---|---|
| 2,386,830 | 10/1945 | Wright | 23/230 R |
| 2,518,307 | 8/1950 | Groebe | 260/671 C |
| 3,420,753 | 1/1969 | Happel et al. | 23/230 R |
| 3,579,551 | 5/1971 | Craddock et al. | 260/413 |
| 3,816,489 | 6/1974 | Craddock et al. | 260/413 |
| 3,852,346 | 12/1974 | Forster et al. | 260/413 |
| 3,948,965 | 4/1976 | Cawse | 260/449 R |
| 3,952,039 | 4/1976 | Walker et al. | 260/449 R |
| 3,957,857 | 5/1976 | Pruett et al. | 260/449 R |

OTHER PUBLICATIONS
The Review of Scientific Instruments vol. 43, No. 7; July 1972 pp. 1024–1026 – H. B. Tinker et al.
Inorganic Chemistry vol. 11, No. 3, 1972 pp. 473–475 – Denis Forster.

*Primary Examiner*—Winston A. Douglas
*Assistant Examiner*—P. E. Konopka
*Attorney, Agent, or Firm*—Joseph D. Kennedy

[57] ABSTRACT

The present invention relates to an improved process for the preparation of carboxylic acids, specifically by the reaction of ethylenically unsaturated compounds with carbon monoxide and water, in the presence of catalyst compositions essentially comprising iridium compounds and complexes, together with an iodide promoter, the improvement being the provision of at least 50 percent by weight of the iridium in the reaction solution in a highly catalytically active form as a species having infrared absorption bands at 2098 $cm^{-1}$ (vs), 2155 $cm^{-1}$ (w), 2180 $cm^{-1}$ (vw, br). By monitoring the infrared absorption spectra of reacting solutions and following the magnitude of the 2098 $cm^{-1}$ band the operating conditions are adjusted so that this band is present in 50 percent or more concentration relative to the infrared absorption spectral bands of the other iridium species in solution. Through this monitoring and control process significantly increased reactor productivity to carboxylic acids is achieved.

9 Claims, No Drawings

PRODUCTION OF CARBOXYLIC ACIDS BY CONTROLLING THE ACTIVE FORM OF IRIDIUM CATALYST IN RESPONSE TO INFRARED ABSORPTION SPECTRA

This invention relates to an improved process for the preparation of carboxylic acids. More particularly, it relates to an improved process for the reaction of ethylenically unsaturated compounds with carbon monoxide and water in the presence of catalyst compositions essentially comprising iridium compounds and complexes and an iodide promoter to yield carboxylic acids selectively and with very high productivity for the catalyst system. This very high catalyst system productivity (i.e., productivity in g-moles of product formed/liter of reaction solution-hr-gm of iridium) is achieved by having 50 percent or more of the iridium in the reaction solution in its highly catalytically active form, as defined herein. The approximate formula for the highly active form is proposed as $[(HIr(CO)_2I_2(H_2O)]$. This species together with the other iridium species present in the iridium containing reaction solution can be characterized by examination of the infrared spectrum in the 1800–2200 $cm^{-1}$ region where metal carbonyls and hydrides absorb. These spectra may be obtained using a standard infrared spectrometer such as a Beckman IR-12 spectrometer. The highly catalytically active specie, formulated as $[(HIr(CO)_2I_2(H_2O)]$, has an infrared absorption spectrum in reaction solution of 2098 $cm^{-1}$ (vs), 2155 $cm^{-1}$ (w) and 2180 (vw,br). In the present terminology vs refers to very strong, w refers to weak, vw is very weak and br refers to broad. By monitoring the strongest of these peaks, 2098 $cm^{-1}$, in the reaction solution (e.g., analyzing with the employment of a high temperature-high pressure infrared absorption spectral cell) it has now been found possible to control the operating conditions (e.g., temperature, pressure, water concentration, and iodide concentration) in a feedback manner such that the 2098 $cm^{-1}$ band is present in 50 percent or more concentration relative to the other iridium species. A feedback control method such as this with the 2098 $cm^{-1}$ infrared band being the detected signal and the controller signal adjusted on the operating parameters represents a practical and economical method for best utilization of the expensive iridium-iodide catalyst system.

The prior art (U.S. Pat. No. 3,579,551) teaches the carbonylation of ethylenically unsaturated compounds to carboxylic acids employing an iridium/iodide catalyst system. This patent described that a number of forms or iridium and iodide may be employed as precursors to the actual catalytic form in solution. It has now been found that several different iodocarbonyliridium complexes are present in the reaction solution depending on the operating conditions of the reactor. It has further been discovered that when one of these complexes, characterized as the neutral iodocarbonyl iridium (III) hydride having infrared absorption bands at 2098 $cm^{-1}$ (vs), 2155 $cm^{-1}$ (w) and 2180 $cm^{-1}$ (vw,br) and the approximate formula $[(HIr(CO)_2I_2(H_2O)]$ is present in at least 50 percent or greater concentration by weight relative to the total iridium present in solution, a very high productivity to carboxylic acid is found to be achieved.

To specify the specific operating conditions of temperatures, pressure, water concentration, and iodide concentration at which this very high productivity occurs is extremely difficult due to the complex interaction of these parameters on the reaction kinetics. A prohibitive number of experiments would be required to establish the preferred combination of all the variables of the reaction system. This disadvantage has now been found to be overcome by monitoring the infrared absorption spectra of the reaction solution and employing feedback control of the operating conditions so as to have a high proportion of the expensive iridium in the preferred form (i.e., having the major band at 2098 $cm^{-1}$). When this is accomplished a high productivity of the iridium to the desired carboxylic acid product is found to be achieved.

Infrared absorption spectra of the reaction solution can be carried out on samples removed from the reactor and placed in standard liquid cells at ambient conditions or, preferably, through the use of an in situ high temperature-high pressure spectral cell as described in THE REVIEW OF SCIENTIFIC INSTRUMENTS, 43, No. 7, July 1972, pg. 1024. The latter procedure allows a portion of the reacting solution at operating conditions to be continuously fed through the cell and its infrared spectra measured. From the peak height of the 2098 $cm^{-1}$ band relative to the peak height of the other less reactive iridium species, operating conditions are controlled such that the predominant form of the iridium is that corresponding to the 2098 $cm^{-1}$ band in the infrared spectra and thus the optimum productivity is obtained.

In addition to the iridium complex formulated as $[HIr(CO)_2I_2(H_2O)]$ which catalytically has been found to produce carboxylic acid at very high productivity, a partial list of other reactive (but to a lesser degree) iridium carbonyl compounds which have been identified in the reacting solution are listed below with their corresponding absorption.

Table 1

| Compound | Infrared Absorption ($cm^{-1}$) |
|---|---|
| $HIr(CO)_2I_2(H_2O)$ | 2180 (vw, br), 2155 (w), 2098 (vs) |
| $Ir(CO)_3I$ | 2076 (vs), 2042 (s) |
| $Ir(CO)_3I_3$ | 2186 (w), 2170 (vw), 2132 (vs) |
| $Ir(CO)_2I_2^-$ | 2049 (vs), 1973 (vs) |
| $Ir(CO)_2I_4^-$ | 2115 (vs), 2070 (vs) |
| $HIr(CO)_2I_3^-$ | 2160 (w, br), 2107 (vs) |

It should be noted that no other iridium species has the very strong infrared spectral band at 2098 $cm^{-1}$ so that it is especially feasible to control the reactor operation for high productivity to carboxylic acid employing the measurement of this peak.

In accordance with the present invention, ethylenically unsaturated compounds are converted selectively to carboxylic acids by reaction in the liquid phase with carbon monoxide and water at temperatures from about 125° C to 225° C, and at partial pressures of carbon monoxide from 0.35 kg/cm² to 210 kg/cm², peferably 17 kg/cm² to 70 kg/cm², although higher pressure may be employed, in the presence of a catalyst system comprised of an iridium containing component, and a promoter portion, i.e., an iodide. The iodide may be derived from iodide or iodine compounds. The present process is particularly advantageous at lower pressures, although higher pressures may also be used.

The iridium portion of the catalyst system is prepared from iridium species such as iridium metal, simple iridium salts, organoiridium compounds, and coordination compounds of iridium, specific examples of which may be taken over from the following partial list of suitable compounds.

Ir metal
IrCl$_3$
IrBr$_3$
IrI$_3$
IrCl$_3$·3H$_2$O
IrBr$_3$·3H$_2$O
Ir(CO)$_4$Cl$_2$
Ir$_2$(CO)$_4$Br$_2$
Ir$_2$(CO)$_4$I$_2$
Ir$_4$(CO)$_{12}$
Ir[(C$_6$H$_5$)$_3$P]$_2$(CO)I
Ir[(C$_6$H$_5$)$_3$P]$_2$(CH$_3$I)$_2$
Ir(SnCl$_3$)[(C$_6$H$_5$)$_3$P]$_3$
IrCl(CO)[(C$_6$H$_5$)$_3$As]$_2$
IrI(CO)[(C$_6$H$_5$)$_3$Sb]$_2$
Ir[(C$_6$H$_5$)$_3$P]$_2$(CO)Cl
IrCl[(C$_6$H$_5$)$_3$P]$_3$H$_2$
[(n-C$_4$H$_9$)$_4$N][Ir(CO)$_2$X$_2$]
where X = Cl$^-$, Br$^-$, I$^-$
[(n-C$_4$H$_9$)$_4$As]$_2$[Ir$_2$(CO)$_2$Y$_4$]
where Y = Br$^-$, I$^-$
[(n-C$_4$H$_9$)$_4$P][Ir(CO)I$_4$]
Ir[(C$_6$H$_5$)$_3$P]$_2$(CO)Br
Ir[(n-C$_4$H$_9$)$_3$P]$_2$(CO)Br
Ir[(n-C$_4$H$_9$)$_3$P]$_2$(CO)I
IrBr[(C$_6$H$_5$)$_3$P]$_3$
IrI[(C$_6$H$_5$)$_3$P]$_3$
IrCl[(C$_6$H$_5$)$_3$P]$_3$
[(C$_6$H$_5$)P]$_3$Ir(CO)H
Ir[(C$_2$H$_4$)$_2$Cl]$_2$
K$_4$Ir$_2$Cl$_2$(SnCl$_3$)$_4$
K$_4$Ir$_2$Br$_2$(SnBr$_3$)$_4$
K$_4$Ir$_2$I$_2$(SnI$_3$)$_4$
IrO$_2$
K$_3$Ir(NO$_2$)$_6$ The second component of the catalyst system consists of iodide and may be supplied as the free iodine or iodide compounds such as hydrogen iodide, alkyl- or aryl-iodide preferably having the same number of carbon atoms as the feedstock), metal iodide, ammonium, phosphonium, arsonium, stibonium iodide, etc., and may be the same or different from any halogen component already present in the precursor iridium component of the catalyst system. Iodine or iodide compounds are suitable for the promoter portion of the catalyst, but those containing iodide are preferred. Accordingly, suitable compounds providing the promoter portion of the catalyst system of this invention may be selected from the following list of preferred iodine and/or iodine-containing compounds:

RI$_n$ (n is 1–3)
where
R = an alkyl-, alkylene or aryl-group of 1 to 18 carbon atoms e.g., CH$_3$I, C$_6$H$_5$I, CH$_3$CH$_2$ICH$_2$CH$_2$I, etc. other examples include I$_2$; I$_3^-$ HI; and $$\underset{O}{\overset{\phantom{O}}{R\!-\!\overset{\|}{C}\!-\!I}}$$

where
R = alkyl- or aryl-group, e.g., $$\underset{O}{\overset{\phantom{O}}{CH_3\!-\!\overset{\|}{C}\!-\!I}}$$

R$_4$MI, R$_4$MI$_3$, or R$_2$MI$_2$
where
R = hydrogen or an alkyl- or aryl-group of 1 to 18 carbon atoms e.g., NH$_4$I, PH$_4$I$_3$, PH$_3$I$_2$,
M = N, P, As or Sb(C$_6$H$_5$)$_3$PI$_2$, and/or combinations of R, M, and I.

The concentration of the iodide component of the catalyst system may vary widely over the broad concentration range of 10$^{-6}$ moles/liter to 18 moles/liter, based on iodide atom. In the process of this invention, however, the preferred concentration range of promoter is 10$^{-4}$ moles/liter to 2 moles/liter of catalyst solution.

The preparation of the active catalyst complex which includes both iridium and iodide promoter components may be accomplished by a variety of methods. However, it is thought that a substantial part of the precursor medium component is converted to the monovalent state during the preparative treatment. In general, in the process of this invention, it is possible to preform the active carbonylation catalyst system which contains both iridium and iodide promoter components. For example, to prepare the catalyst system, the first component of the catalyst system, e.g., finely divided iridium metal (powder), a simple iridium salt or iridium compound as a precursor is dissolved in a suitable medium, and carbon monoxide is bubbled through the above iridium solution, preferably while maintaining gentle heating and stirring of the iridium solution. Then an acidic solution of the desired promoter source is added to form an active catalytic solution containing the necessary iridium and iodide promoter components.

Generally, the active catalyst containing the iridium and promoter components of the catalyst system of this invention may be preformed prior to charging the reactor, or it may be formed in situ in the reactor as discussed above. For example, to prepare the catalyst system, the first component of the catalyst system, e.g., an iridium salt such as IrCl$_3$·3H$_2$O is dissolved in a suitable solvent such as 2-methoxyethanol. Subsequently, carbon monoxide is bubbled through the solution where an intermediate is produced where in the iridium is in the monovalent state. The second or promoter component is, for example, added to the above solution: e.g., as aqueous HI, elemental iodine, alkyl iodide (with alkyl radicals of 1 to 30 carbon atoms) or other iodine containing compound.

Alternatively, the iridium precursor, e.g., Na$_2$IrCl$_6$, Na$_2$IrBr$_6$ or [Ir(CO)$_3$Cl]$_2$, may be dissolved in 2-methoxyethanol containing a dilute aqueous acid, e.g., HCl, acetic acid, etc., as solvent. Then the solution of the iridium compound is heated, for example, to 60° C–80° C, or in general at a temperature below the boiling point of the solvent with stirring. A reducing agent such as carbon monoxide is bubbled through the said solution to obtain the iridium component at least in part in the monovalent state. Subsequently, the iodine promoter is added as described herein, although the iodine containing promoter may also be added first.

Another embodiment of the present invention employs compounds of monovalent iridium initially, wherein compounds such as [Ir(CO)$_3$I] are dissolved in a suitable solvent that is preferably warmed and stirred. Subsequent addition of an acidic solution of the halogen promoter, e.g., alkyl iodide, elemental iodine, aqueous HI, etc., results in formation of an active carbonylation catalyst solution.

Alternate embodiments of the present invention include use of other iridium components in various oxidation states and ligand environments, e.g., iridium metal (zero valence state), iridium salts, e.g., $IrCl_3$ (+3 valence state), other iridium compounds, e.g., iridium acetylacetonate (+3 valence state), etc.; with suitable chemical reagents to accomplish the desired transformation of the iridium precursor to an active catalytic complex species. Such reagents include reducing agents, e.g., hydrogen, carbon monoxide, hydrazine, formic acid, phenyl-hydrazine, etc.; and oxidizing agents, e.g. elemental halogens $I_2$ or $Br_2$), mineral acids (HCl, HBr, $HNO_3$, HI), peroxides ($H_2O_2$, cumene hydroperoxide, etc.).

The liquid reaction medium employed may be any solvent compatible with the catalyst system and may include pure olefins or saturated or unsaturated, e.g., benzene, decane, eicosane, etc. Mixtures thereof with the desired carboxylic acids such as nonanoic acid may be used. The preferred solvent and liquid reaction medium for the process of this invention is a monocarboxylic acid having 2 to 20 carbon atoms, e.g., acetic, propionic, hexanoic, decanoic, dodecanoic, naphthoic, oleic, and elaidic acids, including isomeric forms. Water may optionally be added to the reaction mixture in excess of the stoichiometric quantity discussed below.

The present invention is based upon the production of carboxylic acids by the transformation of an ethylenically unsaturated compound, having from 2 to 30 carbon atoms, and containing the structural unit

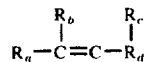

in heterocyclic, heteroaliphatic, aliphatic, acyclic, cyclic or polycyclic hydrocarbon form, where $R_a$, $R_b$, $R_c$, and $R_d$ are moieties having from 0 to 20 carbon atoms and being selected from the group consisting of hydrogen, halogen, alkyl, alkene, aryl, cycloalkyl and cycloalkene moieties, the said heterocompounds being substituted with nitrogen, phosphorus, sulfur, halogen, or oxygen atoms.

Suitable feedstocks in the process of this invention are any ethylenically unsaturated compounds. Suitable compounds include ethylene, propylene, butene-1; butene-2; hexenes; octenes; dodecenes; hexadecene; 2-methylpropene; 1,3-butadiene; 2-methyl-1,3-butadiene; 2,3-dimethyl-1,3-butadiene; cyclohexene; methylcyclohexene; styrene; methylstyrene; vinylcyclohexene; 3,3-dimethyl-1-butene; 1,4-hexadiene; 2,4-hexadiene; 1,5-hexadiene; 2-methyl-1,4-hexadiene; acrolein; methylvinyl ketone; allyl alcohol; 2-phenylbutene; cyclopentadiene; 2-cyclohexylbutene; allene; allylamine; diallylamine; methylacrylate; and mixtures thereof.

A typical carbonylation reaction selective to carboxylic acid requires at least one mole of carbon monoxide and one mole of water per mole (equivalent) of ethylenically unsaturated linkage reacted. An excess of carbon monoxide and water over the molar quantity equivalent to the number of moles of ethylenically unsaturated linkage reacted may be present. The molar proportion of water is thus at least 1 mole per mole unsaturated feedstock, and up to 20,000 moles of water. An increase of water or iodide is provided by increasing the flow rate of the water or iodide in a continuous process, or by pumping the water or iodide into a batch reactor. The moles of iodide per mole of unsaturated feedstock is from $10^{-6}$ to 0.5 and preferably $10^{-3}$ to $10^{-1}$.

The reactor can be operated either in a batch or continuous manner with respect to the iridium. In the present terminology a batch process refers to one in which essentially all of the iridium remains in the reactor during the reaction time. Following the reaction the product is separated from the iridium which is then reused in a subsequent batch. During the batch reaction time water, olefin, carbon monoxide and iodide may be added to or removed from the reactor. A continuous process refers herein to one in which the iridium is continuously recycled from the separations area (e.g. constant flow of the iridium containing solution out of the reactor to a distillation column where the iridium remains in the heel and is continuously recycled to the reactor).

In the present process when monitoring of the reaction solution shows the species with its major infrared band at 2098 $cm^{-1}$ has fallen below 50 percent restoration of the high productivity of the iridium catalyst is accomplished by making at least one of the following changes:

1. if the 2076 $cm^{-1}$, and the 2042 $cm^{-1}$ bands have increased, then increase the amount of iodide or increase the temperature 2. if the 2132 $cm^{-1}$ band has increased, then increase the amount of water 3. if the 2115 $cm^{-1}$, and the 2070 $cm^{-1}$ bands have increased, then lower temperature or remove iodide from the reactor.

For a better understanding of the process of the present invention specific embodiments of the process are presented below. These examples and illustrations are not to be construed in any way as limiting the scope of the invention.

EXAMPLE 1

A Hastelloy-C batch reactor is charged with the following ingredients: 0.606 grams of an iridium compound having the formula $IrCl_3\cdot3H_2O$ as catalyst precursor; 4.2 grams of 2-iodooctane as iodide co-catalyst; 77 ml of tridecanoic acid as solvent, and 82 ml of dodecene as feed. The reactor is pressurized with carbon monoxide to a total pressure of 29 kg/cm$^2$ at the reaction temperature of 175° C. The reaction is carried out at constant pressure. Distilled water is pumped into the reaction during the course of the reaction. Liquid samples are removed as the reaction proceeds and their infrared absorption spectra is analyzed on a Perkin-Elmer 221 spectrophotometer employing 0.2 mm $CaF_2$ cells with a reference solution.

The first sample removed after 8 minutes of reaction has 53.7 weight percent dodecene and 0.16 weight percent water. The rate of carboxylic acid production is an excellent 3.3 g-m/1-hr. The infrared spectra shows 70 percent of the iridium in the reaction solution to be the species with the major 2098 $cm^{-1}$ band formulated as [$HIr(CO)_2I_2(H_2O)$]. The remaining 30% is the Ir($CO)_3I$ with infrared bands at 2076 $cm^{-1}$ and 2042 $cm^{-1}$. After a reaction time of 42 minutes the reaction rate slows to 0.6 g-m/1-hr even though gas chromatographic analysis (GC) of the liquid sample shows 30.1 percent dodecene remaining unreacted. The infrared spectra of this sample, however, shows only 20 percent of the iridium in the preferred form corresponding to the 2098 cm$^{-1}$ band. The remainder of the iridium is 60 percent as Ir(CO)$_3$I$_3$ with an infrared band at 2132 cm$^{-1}$ and 10 percent as Ir(CO)$_3$I with infrared bands at 2076 cm$^{-1}$ and 2042 cm$^{-1}$.

Addition of water produces a significant increase in the reaction rate to carboxylic acids. The next sample analyzed by GC analysis has 12.5 percent dodecene, less than half the olefin of the previous sample. However, the rate of tridecanoic acid production increases to 1.2 g-m/1-hr. The infrared absorption spectra shows the reason for this increased productivity of the iridium catalyst system. The iridium specie corresponding to the major 2098 cm$^{-1}$ band now is 80 percent of the total iridium in solution, the remainder mostly the Ir(CO)$_2$I$_4^-$ (bands at 2115 cm$^{-1}$ and 2070 cm$^{-1}$). The final sample is removed from the reactor when the productivity declines to 0.25 g-m/1-hr. Only 4.4 weight percent dodecene is unreacted and the infrared shows 40 percent of the iridium as the 2098 cm$^{-1}$ specie, the rest the Ir(CO)$_2$I$_4^-$ specie.

The results of this experiment are summarized below:

| Sample No. | Wt % Olefin | Wt % Water | Catalyst Productivity (g-m/1-hr) | % of Iridium as Following Specie: | | |
|---|---|---|---|---|---|---|
| | | | | 2098 cm$^{-1}$ | Others | |
| 1 | 53.7 | 0.16 | 3.3 | 70 | 30 | Ir(CO)$_3$I |
| 2 | 30.1 | 0.06 | 0.6 | 20 | 60 | Ir(CO)$_3$I$_3$ |
| | | | | | 10 | Ir(CO$_3$)I |
| 3 | 12.5 | 0.23 | 1.2 | 80 | 20 | Ir(CO)$_2$I$_4^-$ |
| 4 | 4.4 | 0.42 | 0.25 | 40 | 60 | Ir(CO)$_2$I$_4$ |

These results and those of the following examples establish the very high catalytic activity of the iridium iodide catalyst system to carboxylic acid production when at least 50% or more by weight of the iridium in the reaction solution is present as the above described compound with its major infrared absorption band at 2098 cm$^{-1}$. When other iridium species predominate in solution (e.g., Sample 2 with only 20 percent as 2098 cm$^{-1}$), the productivity for the carbonylation of olefins to carboxylic acids significantly decreased.

EXAMPLE 2

The experimental conditions of Example 1 are repeated except that 0.303 grams of IrCl$_3$·3H$_2$O and 3.1 grams of 2-iodooctane are employed and the reaction temperature is 185° C.

The results of this experiment are summarized below:

| SAMPLE NO. | WT % OLEFIN | WT % WATER | CATALYST PRODUCTIVITY (g-m/1-hr) | % OF IRIDIUM AS FOLLOWING SPECIES: | | |
|---|---|---|---|---|---|---|
| | | | | 2098 cm$^{-1}$ | Others | |
| 1 | 55.7 | 0.06 | 0.2 | 10 | 70 | Ir(CO)$_3$I$_3$ |
| | | | | | 20 | Ir(CO)$_3$I |
| 2 | 38.5 | 0.24 | 1.1 | 60 | 40 | Ir(CO)$_3$I |

At Sample 2 the productivity of the catalyst system is over 5 times greater than in Sample 1 even though the olefin reactant concentration decreases. The higher productivity in Sample 2 corresponds to the 6-fold increase in the quantity of the specie with major band at 2098 cm$^{-1}$, formulated as [HIr(CO)$_2$I$_2$(H$_2$O)], in the reaction solution.

EXAMPLE 3

The experimental conditions are those of Example 2 except 2.1 grams of 2-iodooctane and 1.0 grams of trioctylphosphine oxide are employed.

The results of this experiment are as follows:

| SAMPLE NO. | WT % OLEFIN | CATALYST PRODUCTIVITY (q-m/1-hr) | % OF IRIDIUM As FOLLOWING SPECIES: | | |
|---|---|---|---|---|---|
| | | | 2098 cm$^{-1}$ | Others | |
| 1 | 55 | 1.5 | 80 | 10 | Ir(CO)$_2$I$_4^-$ |
| 2 | 27.8 | 0.75 | 50 | 50 | Ir(CO)$_2$I$_4^-$ |
| 3 | 16.5 | 0.18 | 0 | 90 | Ir(CO)$_2$I$_4^-$ |

The above results demonstrate the significant decrease in the catalyst productivity which occurs when the quantity of iridium corresponding to the major 2098 cm$^{-1}$ band drops below 50 percent. While the decrease in olefin concentration is less than one-half between Samples 2 and 3, the productivity to carboxylic acids drops 4-fold, in line with the disappearance of the 2098 cm$^{-1}$ band in the infrared absorption spectra of Sample 3.

EXAMPLE 4

The example conditions of Example 2 are repeated except that 0.52 grams of IrI$_3$·XH$_2$O is employed as the catalyst precursor. No other iodide source is used so that the IrI$_3$·H$_2$O serves as the precursor of both the iridium and iodide components of the catalyst system.

A liquid sample removed after 25 minutes at reaction conditions analyzes as over 50 weight percent of the unreacted olefin feed, and has 0.16 weight percent water. The reaction rate is slow at 0.2 g-m/1-hr. Infrared analysis of this sample shows no iridium at the major 2098 cm$^{-1}$ band. Essentially all of the iridium is present as the neutral iridium(I) specie, Ir(CO)$_3$I.

The reaction was continued for 110 minutes with no change in the observed reaction rate to tridecanoic acid. At this time 2.8 grams of 58 percent aqueous hydroiodic acid was added to the reaction solution. The rate of the reaction more than tripled to 0.65 g-m/1-hr. The infrared analysis of this sample now has 50 percent of the iridium at the 2098 cm$^{-1}$ band with the remaining 50 percent split between Ir(CO)$_3$I and Ir(CO)$_2$I$_4^-$.

This experimental result shows the improvement in the catalyst system productivity by addition of iodide to increase the quantity of the iridium component at the 2098 cm$^{-1}$ band to 50 percent. At less than 50 percent of this species a significantly lower reaction to carboxylic acid occurs.

In further experiments, other olefins (e.g., ethylene, propylene, hexene-1, isomerized hexenes, octenes and eicosene) both alpha and internal are employed as the unsaturated reactant with similar results to those above. Other operating parameters besides olefin concentration, water concentration, and iodide concentration as described in Examples -4 (e.g., temperature, carbon monoxide pressure, additives) are also varied. While complex kinetic interactions on reaction rate are observed among these operating parameters, it is found that maintaining 50% or greater of the iridium components in solution as the specie with its major infrared absorption band at 2098 cm$^{-1}$ gives superior productivity for this expensive noble metal catalyst system.

EXAMPLE 5

A continuous pilot plant is operated for the production of heptanoic acid from hexene, carbon monoxide, and water. The reactor is operated at 180° C and a total pressure of 37 kgm/cm$^2$. Makeup hexene, carbon monoxide, and water are added to the recycle streams containing iridium, hexyl iodide, hydrogen iodide, hexene, heptanoic acid, and water. The liquid reactor effluent is continuously monitored by an in situ infrared absorption spectrophotometer. The peak heights of all iridium species in solutions are measured. Controllers are set on the makeup water flow rate such that the peak at 2098 cm$^{-1}$ is maintained at 50 percent or more of the total peaks corresponding to iridium species on the infrared trace. If control of water flow rate is insufficient to maintain this operation with the required percentage of the 2098 cm$^{-1}$ peak a back-up controller on the iodide flow rate is employed.

Similar iridium and iodide containing catalysts can function as catalysts for alcohol carbonylation to carboxylic acids, e.g. methanol to acetic acid. The infrared spectra of such systems under reaction conditions is quite different from that discussed above for olefin hydrocarboxylation. In particular under high reaction ratio conditions a species with strong bands at 2100 to 2042 cm$^{-1}$ is observed.

EXAMPLE 6

A batch reactor is operated for the production of decanoic acid from nonene, carbon monoxide and water. The reactor is operated at 180° C and a total pressure of 37 kgm/cm$^2$. Early in the batch cycled the liquid reaction solution is analyzed employing an infrared spectrophotometer. The infrared spectra shows less than 50 percent of the iridium present having the desired 2098 cm$^-$ band. The dominant bands are at 2076 cm$^{-1}$ and 2042 cm$^{-1}$. The iodide content of the reactor is doubled by adding 2-iodononane. The reaction rate increases four fold and the 2098 cm$^{-1}$ band in the sample removed from the reactor now has 80 percent of the iridium species present in solution. Instead of increasing the iodide content of the reactor in increase in temperature to 200° C also increases the intensity of the 2098 cm$^{-1}$ band.

As olefin, water and carbon monoxide are consumed during the batch cycle the rate of reaction decreases and the next liquid sample from the reactor analyzed by infrared shows less than 20 percent of the iridium corresponding to the 2098 cm$^{-1}$ band with over 70 percent of the iridium as the Ir(CO)$_3$I$_3$ with infrared absorption band at 2132 cm$^{-1}$. Rate of water addition to the reactor is increased and the reaction rate triples. The liquid sample removed from the reactor now has 70 percent of the iridium with the infrared band at 2098 cm$^{-1}$.

After 2 hours batch time the nonene content of the reaction liquid has dropped to 20 weight percent. The reaction rate has decreased to 0.6 g-m/l-hr. The iridium in solution as determined by infrared analysis of a liquid sample has 30 percent of the species at the 2098 cm$^{-1}$ band with the rest predominantly having infrared bands at 2115 cm$^{-1}$ and 2070 cm$^{-1}$. Half of the iodide is removed from the reactor via vaporization and the reaction rate increases to 1.3 g-m/l-hr. An infrared analysis of a liquid sample from the reactor shows the preferred iridium species with its major band at 2098 cm$^{-1}$ has increased so that it is now 75 percent of the iridium species in solution. Instead of removing iodide from the reactor a decrease in temperature to 165° C also increases the intensity of the preferred iridium species with its major infrared spectral band at 2098 cm$^{-1}$.

Through monitoring the infrared spectra of liquid samples removed from the reactor during the batch cycle the above example demonstrates that it is possible to adjust the quanitities of iodide and water and temperature such that the iriduim specie with its major infrared band at 2098 cm$^{-1}$ is maintained at 50 percent or greater of the iridium present in the reacting solution thus keeping batch cycle time to a minimum. Without the monitoring of the infrared spectra of the iridium species much slower reaction rates occur during the batch reaction cycle, as shown above, leading to poorer utilization of the expensive iridium and the necessity for larger pressure reactor facilities.

What is claimed is:

1. In a process for the production of carboxylic acids by the reaction of olefin feedstock compounds having from 2 to 30 carbon atoms, which comprises contacting the said compounds with carbon monoxide and water at a temperature of 125° C to 225° C in the presence of catalyst compositions of iridium compounds or complexes, and iodide, the improvement of maintaining at least 50 percent by weight of the iridium in the reaction solution in a form, which is characterized by having an infrared absorption band at 2098 cm$^{-1}$ by a procedure which comprises increasing the amount of iodide when the 2076 cm$^{-1}$ and 2042 cm$^{-1}$ bands have increased.

2. Process as in claim 1 in which the feedstock is ethylene.

3. Process as in claim 1 in which the feedstock is a distillation cut of C$_6$ to C$_{14}$ carbon atoms.

4. The process of claim 1 wherein at least a stoichiometric proportion of water and carbon monoxide are present.

5. In a process for the production of carboxylic acids by the reaction of olefin feedstock compounds having from 2 to 30 carbon atoms, which comprises contacting the said compounds with carbon monoxide and water at a temperature of 125° C to 225° C in the presence of catalyst compositions of iridium compounds or complexes, and iodide, the improvement of maintaining at least 50 percent by weight of the iridium in the reaction solution in a form, which is characterized by having an infrared absorption band at 2098 cm$^{-1}$ by a procedure which comprises increasing the temperature when the 2076 cm$^{-1}$ and 2042 cm$^{-1}$ bands have increased.

6. In a process for the production of carboxylic acids by the reaction of olefin feedstock compounds having from 2 to 30 carbon stoms, which comprises contacting the said compounds with carbon monoxide and water at a temperature of 125° C to 225° C in the presence of catalyst compositions of iridium compounds or complexes, and iodide, the improvement of maintaining at least 50 percent by weight of the iridium in the reaction solution in a form, which is characterized by having an infrared absorption band at 2098 cm$^{-1}$ by a procedure which comprises increasing the amount of water when the 2132 cm$^{-1}$ band has increased.

7. In a process for the production of carboxylic acids by the reaction of olefin feedstock compounds having from 2 to 30 carbon atoms, which comprises contacting the said compounds with carbon monoxide and water at a temperature of 125° C to 225° C in the presence of catalyst compositions of iridium compounds or complexes, and iodide, the improvement of maintaining at least 50% by weight of the iridium in the reaction solution in a form, which is characterized by having an infrared absorption band at 2098 cm$^{-1}$ by a procedure which comprises lowering the temperature when the 2115 cm$^{-1}$ and 2070 cm$^{-1}$ bands have increased.

8. In a process for the production of carboxylic acids by the reaction of olefin feedstock compounds having from 2 to 30 carbon atoms, which comprises contacting the said compounds with carbon monoxide and water at a temperature of 125° C to 225° C in the presence of catalyst compositions of iridium compounds or complexes, and iodide, the improvement of maintaining at least 50 percent by weight of the iridium in the reaction solution in a form, which is characterized by having an infrared absorption band at 2098 cm$^{-1}$ by a procedure which comprises removing iodide from the reactor when the 2115 cm$^{-1}$ and 2070 cm$^{-1}$ bands have increased.

9. In a method for the production of carboxylic acids by the reaction of olefin feedstock compounds having from 2 to 30 carbon atoms, which comprises contacting the said compounds with carbon monoxide and water at a temperature of 125° C to 225° C in the presence of catalyst compositions essentially composed of iridium compounds or complexes, and iodide, the improvement which comprises providing at least 50% by weight of the iridium in the reaction solution in a form, characterized by having an infrared absorption band at 2098 cm$^{-1}$, and when the course of the reaction causes the proportion of the iridium in said form in the reaction solution to fall below 50% by weight as indicated by the infrared absorption bands, thereafter increasing the said proportion of iridium in said form to at least 50 percent by weight by a procedure which comprises increasing the amount of iodide when the 2076 cm$^{-1}$ and 2042 cm$^{-1}$ bands have increased.

* * * * *